United States Patent
Berberich et al.

(10) Patent No.: US 12,035,955 B2
(45) Date of Patent: Jul. 16, 2024

(54) ALIGNMENT DEVICE FOR A PERIACETABULAR OSTEOTOMY

(71) Applicant: MEDACTA INTERNATIONAL SA, Castel San Pietro (CH)

(72) Inventors: Sascha Berberich, Castel San Pietro (CH); Matteo Ferrari, Castel San Pietro (CH); Matteo Ponzoni, Castel San Pietro (CH); Francesco Siccardi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 728 days.

(21) Appl. No.: 17/281,899

(22) PCT Filed: Oct. 1, 2019

(86) PCT No.: PCT/IB2019/058330
§ 371 (c)(1),
(2) Date: Mar. 31, 2021

(87) PCT Pub. No.: WO2020/070637
PCT Pub. Date: Apr. 9, 2020

(65) Prior Publication Data
US 2021/0346076 A1  Nov. 11, 2021

(30) Foreign Application Priority Data
Oct. 2, 2018 (IT) ........................ 102018000009083

(51) Int. Cl.
*A61B 17/90* (2006.01)
*A61B 17/00* (2006.01)
*A61B 17/68* (2006.01)

(52) U.S. Cl.
CPC .............. *A61B 17/90* (2021.08); *A61B 17/68* (2013.01); *A61B 2017/00477* (2013.01); *A61B 2017/00526* (2013.01); *A61B 2017/681* (2013.01)

(58) Field of Classification Search
CPC .................... A61B 17/90; A61B 17/68; A61B 2017/00477; A61B 2017/681
See application file for complete search history.

(56) References Cited

U.S. PATENT DOCUMENTS

| | | |
|---|---|---|
| 2014/0074099 A1 | 3/2014 | Vegneron et al. |
| 2018/0049749 A1 | 2/2018 | Wu et al. |

FOREIGN PATENT DOCUMENTS

| | | |
|---|---|---|
| JP | 2010504833 A | 2/2010 |
| JP | 2019024741 A | 2/2019 |

(Continued)

OTHER PUBLICATIONS

English Translation of Notice of Reasons of Refusal in JP 2021-518187, dates Apr. 18, 2022, 14 pages.

(Continued)

*Primary Examiner* — Zade Coley
*Assistant Examiner* — Diana Jones
(74) *Attorney, Agent, or Firm* — Meunier Carlin & Curfman LLC

(57) ABSTRACT

Various implementations include an alignment device for carrying out a periacetabular osteotomy operation on a patient that includes
a patient-specific acetabular unit, to be fixed in a univocal position on the iliac bone, in proximity of the acetabulum;
a patient-specific iliac unit, to be fixed in a univocal position on the iliac bone, in a lateral position with respect to the acetabular unit; and
a patient-specific bridge, to be connected in a rigid and univocal manner to the acetabular unit and to the iliac unit.

(Continued)

The acetabular unit and the iliac unit assume a first mutual position incompatible with the bridge. When osteotomy is carried out and the bridge is connected to the acetabular unit and the iliac unit, they assume a second position, different from the first position and corresponding to a bio-mechanically correct position of the acetabulum with respect to the remaining portion of the iliac bone.

20 Claims, 7 Drawing Sheets

(56) References Cited

FOREIGN PATENT DOCUMENTS

RU          2322204 C1     4/2008
WO    WO-2012158917 A1 *  11/2012   ......... A61B 17/1617

OTHER PUBLICATIONS

International Search Report and Written Opinion for International Application No. PCT/IB2019/058330 dated Dec. 12, 2019, 10 pages.

* cited by examiner

ALIGNMENT DEVICE FOR A PERIACETABULAR OSTEOTOMY

The present invention relates to an alignment device for periacetabular osteotomy.

Periacetabular osteotomy is a surgical procedure that has to be performed to treat hip dysplasia, a condition in which the hip joint develops abnormally so that the head of the femur gradually becomes dislodged from the acetabulum.

The hip joint is formed from the acetabular capsule (concave component) and the head of the femur (convex component). When hip dysplasia occurs, the head of the femur does not fit firmly in the acetabulum and easily becomes dislocated. Thus, the two parts (concave and convex) of the joint do not fit together perfectly and this can result in a state of general instability of the articular system, making the hip very susceptible to dislocation.

Periacetabular osteotomy, or PAO, is a highly specialised technique for realigning the acetabulum that has evolved over many years, the purpose of which is to restore the physiological morphology of the joint.

The objective of the surgical treatment of dysplasia is to restore congruency of the joint and thus normal biomechanical forces: periacetabular osteotomy is performed to increase the area of contact between the acetabular capsule and the head of the femur, to reduce instability-related stress, and to normalise load forces.

Periacetabular osteotomy involves cutting the bone around the acetabulum and detaching it completely from the iliac bone, while maintaining the continuity of the bone between the upper part and the lower part of the iliac bone. Once the osteotomies are complete, the acetabular fragment is completely mobile and is reoriented in order to gain the required lateral coverage and angle of version under intra-operative controls with image intensifier. In other words, the acetabulum fragment is translated and reoriented in such a manner that the acetabular cavity is in the most biomechanically correct position. The acetabulum is then fixed again to the iliac bone, usually with the aid of screws and/or metal wires.

The two parts into which the iliac bone has been cut are rotated and realigned by sight. The acetabulum is rotated, while examining antero-posterior projections of the entire pelvis during the operation, until it gains, according to the surgeon, the correct alignment.

This technique produces excellent clinical, radiographic and functional results, by realigning the two parts of the bone in a new and mechanically correct position.

This technique, although highly regarded, is not without possible improvements.

At the moment, periacetabular osteotomy requires a high degree of surgical specialisation and, therefore, long experience. In fact, due to its complexity, the learning curve of the technique is very long. The most complex part of the operation is that relating to the correct alignment of the acetabulum. During this step, there is undoubtedly a high risk of human error.

There is, therefore, a need to simplify periacetabular osteotomy operations and to limit their margin of error as much as possible.

The purpose of the present invention is, therefore, to overcome the drawbacks highlighted above in relation to the prior art.

In particular, one of the tasks of the present invention is to make a device for periacetabular osteotomies that assists the surgeon in the re-alignment phase.

In addition, one task of the present invention is to make a device for periacetabular osteotomies that minimizes the risks for the patient due to human error.

Finally, one of the tasks of the present invention is to make a device for periacetabular osteotomies that allows the surgeon to speed up the operating times.

This purpose and these tasks are achieved by means of an alignment device for periacetabular osteotomies in accordance with claim 1. Other advantages are achieved thanks to the technical features reported in the dependent claims.

These and other features, along with their relative advantages, will be more evident from the illustrative, and therefore non-limiting, description that follows of a preferred, and therefore non-exclusive, embodiment of an alignment device for periacetabular osteotomy in accordance with what is shown in the attached figures, wherein.

Figure 1:
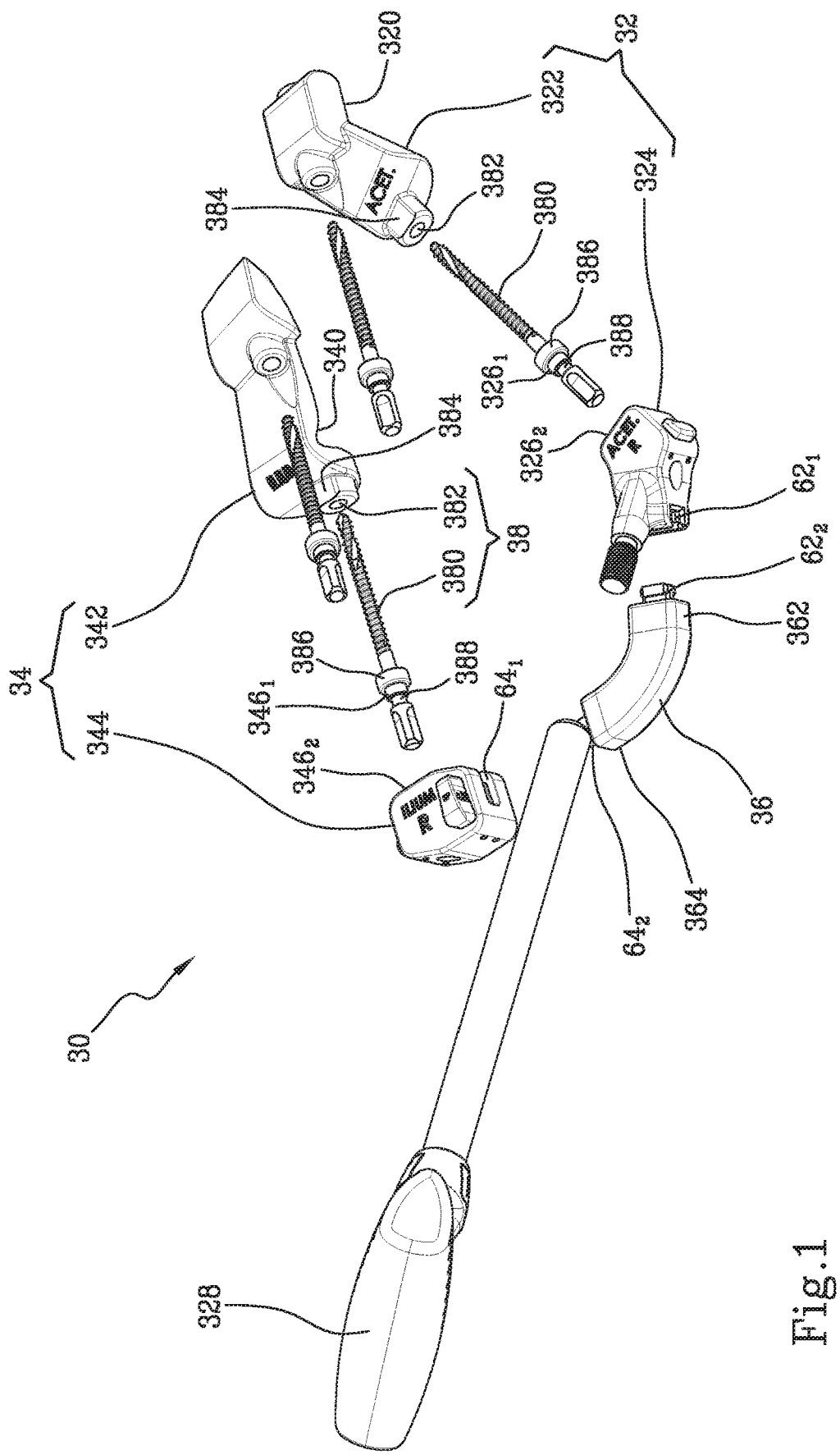
FIG. 1 shows a first exploded view of the alignment device of the invention.

In the context of the present document, some terminological conventions have been adopted in order to make it easier and smoother to read. These terminological conventions are clarified below, also with reference to the attached figures.

The term "patient-specific" means, here and below, a component that is specifically shaped on the basis of the anatomy of a specific patient. In particular, the patient-specific components are designed in a pre-operative step, by means of tools of computer-aided design (CAD), on a three-dimensional model of the bone structure. This model is developed from a three-dimensional image of the patient's bones that is obtained, for example, by computed tomography and/or magnetic resonance imaging. Each patient-specific component is then produced by means of an appropriate computer-aided manufacturing (CAM) technique, such as a machine tool manufacturing technique or one of the so-called three-dimensional printing techniques (additive manufacturing). Therefore, each patient-specific component can be designed and manufactured in such a manner as to define or assume a univocal position with respect to the bone. Patient-specific components are typically made in a single unit, or in a very limited number of units, and are used in one operation only.

The invention relates to an alignment device, indicated as a whole by the number 30, intended to carry out a periacetabular osteotomy operation on a predefined patient. The alignment device 30 comprises:

a patient-specific acetabular unit 32, suitable for being fixed in a univocal position on the patient's iliac bone 80, in proximity of the femur's acetabulum 82;

a patient-specific iliac unit 34, suitable for being fixed in a univocal position on the patient's iliac bone 80, in a lateral position with respect to the acetabular unit 32; and a patient-specific bridge 36, suitable for being connected in a rigid and univocal manner to the acetabular unit 32 and to the iliac unit 34.

In the alignment device 30 according to the invention, when the acetabular unit 32 and the iliac unit 34 are correctly fixed to the intact iliac bone 80, the acetabular unit 32 and the iliac unit 34 assume, the one with respect to the other, a first predefined mutual position incompatible with the simultaneous fixing of the bridge 36 to both the acetabular unit 32 and the iliac unit 34; and when the osteotomy is carried out and the bridge 36 is connected to the acetabular unit 32 and to the iliac unit 34, the acetabular unit 32 and the iliac unit 34 assume, the one with respect to the other, a second predefined mutual position that is different from the first mutual position and corresponding to a bio-mechanically correct position of the acetabulum 82 with respect to the remaining portion of the iliac bone 80. Here and below, the term 'position' refers both to the distance at which a given component is placed with respect to a reference, and to the angular orientation the same component assumes with respect to the same reference. In other words, the position of a single element can be changed either by means of a rigid translation in space, or by means of a rotation on the spot, or by means of a combination of the two movements.

In the alignment device 30 according to the invention, the first mutual position of the acetabular unit 32 and of the iliac unit 34 corresponds, in a univocal manner, to the pathological (i.e. bio-mechanically incorrect) position of the acetabulum 82 with respect to the remaining iliac bone 80. Conversely, the second mutual position of the acetabular unit 32 and the iliac unit 34 corresponds in a univocal manner to the physiological (i.e. bio-mechanically correct) position of the acetabulum 82 with respect to the remaining iliac bone 80.

As mentioned above, the first mutual position of the acetabular unit 32 and the iliac unit 34 is incompatible with the constraints imposed by the bridge 36. In other words, in this first mutual position, the mutual distance and/or the mutual orientation between the acetabular unit 32 and the iliac unit 34 do not allow the bridge 36 to be properly connected to both units 32 and 34 simultaneously. In fact, the shape of the bridge 36, of the acetabular unit 32, and of the iliac unit 34 require that, in order to connect the bridge 36 to both units 32 and 34 simultaneously, the latter must necessarily assume the second mutual position, different from the first mutual position. Preferably, bridge 36, which is also patient-specific, comprises an acetabular end 362 suitable for being connected in a rigid and univocal manner to the acetabular unit 32, and an iliac end 364 suitable for being connected in a rigid and univocal manner to the iliac unit 34.

Advantageously, the acetabular end 362 of the bridge 36 comprises constraint means $62_2$ and the acetabular unit 32 comprises constraint means $62_1$. The constraint means $62_1$ and $62_2$ (collectively also known as the constraint means 62) are complementary, the one with respect to the other, and suitable for creating a mutual rigid and univocal constraint. Advantageously, the iliac end 364 of the bridge 36 comprises constraint means $64_2$ and the iliac unit 34 comprises constraint means $64_1$. The constraint means $64_1$ and $64_2$ (collectively also known as the constraint means 64) are complementary, the one with respect to the other, and suitable for creating a mutual rigid and univocal constraint.

As mentioned above, the acetabular unit 32 and the iliac unit 34 are patient-specific. This technical feature is described in greater detail below. The acetabular unit 32 comprises a rest portion 320 shaped in such a manner as to be perfectly complementary to a specific zone of the surface of the iliac bone 80 identified in the pre-surgery steps. This specific zone of the surface of the iliac bone 80 is identified in proximity to the acetabulum 82. Due to this complementarity, only one correct position is defined for placing the acetabular unit 32 on the surface of the iliac bone 80. Any other position is incorrect and results in a rough and unsteady resting of the acetabular unit 32 on the iliac bone 80. Advantageously, the rest portion 320 of the acetabular unit 32 is at least partially concave. In this way, it can at least partially embrace the front edge of the iliac bone 80. The feature of partial concavity of the rest portion 320 can be better understood, by analogy, considering FIG. 2 and the relative description reported below with reference to the iliac unit 34.

According to one embodiment, the acetabular unit 32 may in turn comprise two sub-units. For example, the acetabular unit 32 may advantageously comprise a patient-specific acetabular base 322 and a general use acetabular interface block 324. In this case, the acetabular base 322 comprises the rest portion 320 and a connecting portion 3261, while the acetabular interface block 324 comprises the constraint means $62_1$ and, in turn, a connecting portion $326_2$. The connecting portion 3261 of the acetabular base 322 and the connecting portion $326_2$ of the acetabular interface block 324 (collectively also called the connecting portions 326) are complementary, the one with respect to the other, and are suitable for establishing a mutual rigid and univocal connection. When the acetabular base 322 and the acetabular interface block 324 are properly connected, the one with respect to the other, in a rigid manner, they form the acetabular unit 32.

The acetabular unit 32 preferably comprises fixing means 38, suitable for fixing the acetabular unit 32 on the iliac bone 80, typically when it is in the correct position. The fixing means 38 preferably comprise at least one bone screw 380 and at least one seat 382 suitable for receiving the bone screw 380. As is well known, the bone screw 380 comprises a threaded shank and a head. The threaded shank is suitable for passing through the seat 382 and fitting firmly into the bone. The screw head is suitable, on the one hand, for providing the grip for a fixing tool (not shown) and, on the other hand, for resting on an abutment surface of the seat 382, so as to define a constraint.

The fixing means 38 preferably comprise two seats 382, each suitable for receiving a bone screw 380. As the experienced person can well understand, each seat 382 defines, in a univocal manner, the insertion direction of the respective screw 380.

Since the seats 382 are part of a patient-specific element (be it the acetabular base 322 alone or the whole acetabular unit 32), the insertion direction of each screw 380 can be defined beforehand, during the pre-surgery steps, in order to obtain the best result in terms of connection.

The acetabular unit 32 preferably comprises a removable handle 328, which can be firmly joined to the acetabular unit 32 so that it can be easily moved despite the encumbrances within the operating field. In fact, as will be better explained later, during a periacetabular osteotomy operation it is necessary to move the acetabulum 82 with respect to the remaining iliac bone 80. The removable handle 328 facilitates this step of the movement.

The same considerations as above for the acetabular unit 32 apply mutatis mutandis to the iliac unit 34 as well. In particular, the iliac unit 34 also comprises a rest portion 340 shaped in such a manner as to be perfectly complementary to a specific zone of the surface of the iliac bone 80 identified in the pre-surgery steps. This specific zone of the surface of the iliac bone 80 is identified in a lateral position with respect to the zone identified for the acetabular unit 32. Due to this complementarity, only one correct position is defined for placing the iliac unit 34 on the surface of the iliac bone 80. Any other position is incorrect and results in a rough and unsteady resting of the acetabular unit 34 on the iliac bone 80. Advantageously, the rest portion 340 of the iliac unit 34 is at least partially concave. In this way, it can at least partially embrace the front edge of the iliac bone 80. One embodiment of the iliac unit 34 comprising a partially concave rest portion 340 is shown in detail in FIG. 2. This figure can also be used to understand, by analogy, the same partial concavity feature when it refers to the rest portion 320 of the acetabular unit.

In accordance with one embodiment, the iliac unit 34 may, in turn, comprise two sub-units. For example, the iliac unit 34 may advantageously comprise a patient-specific iliac base 342 and a general use iliac interface block 344. In this case, the iliac base 342 comprises the rest portion 340 and a connecting portion $346_1$, while the iliac interface block 344 comprises the constraint means $64_1$ and, in turn, a connecting portion $346_2$. The connecting portion $346_1$ of the iliac base 342 and the connecting portion $346_2$ of the iliac interface block 344 (collectively also called connecting portions 346) are complementary, the one with respect to the other, and are suitable for establishing a mutual rigid and univocal connection. When the iliac base 342 and the iliac interface block 344 are properly connected to each other in a rigid manner, they form the iliac unit 34.

The iliac unit 34 preferably comprises fixing means 38, suitable for fixing the iliac unit 34 to the iliac bone 80, typically when it is in the correct position. The fixing means 38 preferably comprise at least one bone screw 380 and at least one seat 382 suitable for receiving the bone screw 380. As is well known, the bone screw 380 comprises a threaded shank and a head. The threaded shank is suitable for passing through the seat 382 and fitting firmly into the bone. The head of the screw 380 is suitable, on the one hand, for providing the grip for a fixing tool (not shown) and, on the other hand, for resting on an abutment surface of the seat 382, so as to define a constraint.

The fixing means 38 preferably comprise two seats 382, each suitable for receiving a bone screw 380. As the experienced person can well understand, each seat 382 defines, in a univocal manner, the insertion direction of the respective screw 380.

Since the seats 382 are part of a patient-specific element (be it the iliac base 342 alone or the whole iliac unit 34), the insertion direction of each screw 380 can be defined beforehand, during the pre-surgery steps, in order to obtain the best result in terms of connection.

The constraint means 62, 64 and/or the connecting portion 326, 346 preferably adopt shape couplings, releasable by means of snap mechanisms. This solution allows the surgeon to obtain a firm and rigid coupling in a short time and without the use of tools.

In addition, the constraint means 62, 64 and/or the connecting portion 326, 346 adopt shape couplings that are preferably different the one from the others and mutually incompatible. This technical feature prevents any error from occurring during the operation, e.g. by turning the bridge 36 upside down with respect to the correct design position. As already mentioned, the bridge 36 comprises:

constraint means $62_2$ at the acetabular end 362 suitable for being connected to the constraint means $62_1$ of the acetabular unit 32, and constraint means $64_2$ at the iliac end 364 suitable for being connected to the constraint means $64_1$ of the iliac unit 34.

By making the constraint means 62, 64 at the two ends of the bridge 36 with different and incompatible shapes, the one with respect to the other, the risk of the bridge 36 being incorrectly placed, during the operation, with the acetabular end 362 towards the iliac unit 34 and with the iliac end 364 towards the acetabular unit 32, is avoided. Such a placement would, in fact, impose a completely incorrect relative position on the acetabular unit 32 and the iliac unit 34.

Similarly, where the acetabular unit 32 and the iliac unit 34 each comprise two sub-units, it is preferable that the connecting portions 346 of the iliac unit 34 are incompatible with the connecting portions 326 of the acetabular unit 32 and vice versa. Even in this case, in fact, it is necessary to avoid the acetabular base's 322 being connected to the iliac interface block 344 and, vice versa, the iliac base's 342 being connected to the acetabular interface block 324.

As an alternative or in addition to the incompatibility between the respective connecting portions 326 and 346, the incorrect connection between a base and an interface block can also be avoided with a clearly marked label on the piece. For this purpose, the attached figures clearly show the letters ACET on the acetabular base 322 and on the acetabular interface block 324, while ILIUM on the iliac base 342 and on the iliac interface block 344.

In the embodiment shown in the attached figures, the connecting portions 326 of the acetabular unit 32 are provided at one seat 382 of a bone screw 380 and are defined as follows. The bush 384 which surrounding the seat 382 defines, for the acetabular interface block 324, a univocal orientation around the axis of the bone screw 380. The head of the screw 380 also comprises a shoulder 386 and a groove 388 that are intended to be housed within the connecting portion $326_2$ of the acetabular interface block 324. The shoulder 386 defines an axial rest that determines a univocal position along the axis of the bone screw 380 for the acetabular interface block 324. The groove 388 of the head of the screw 380 is intended to receive a spring guillotine suitable for firmly holding the connection between the acetabular base 322 and the acetabular interface block 324.

Figure 2:
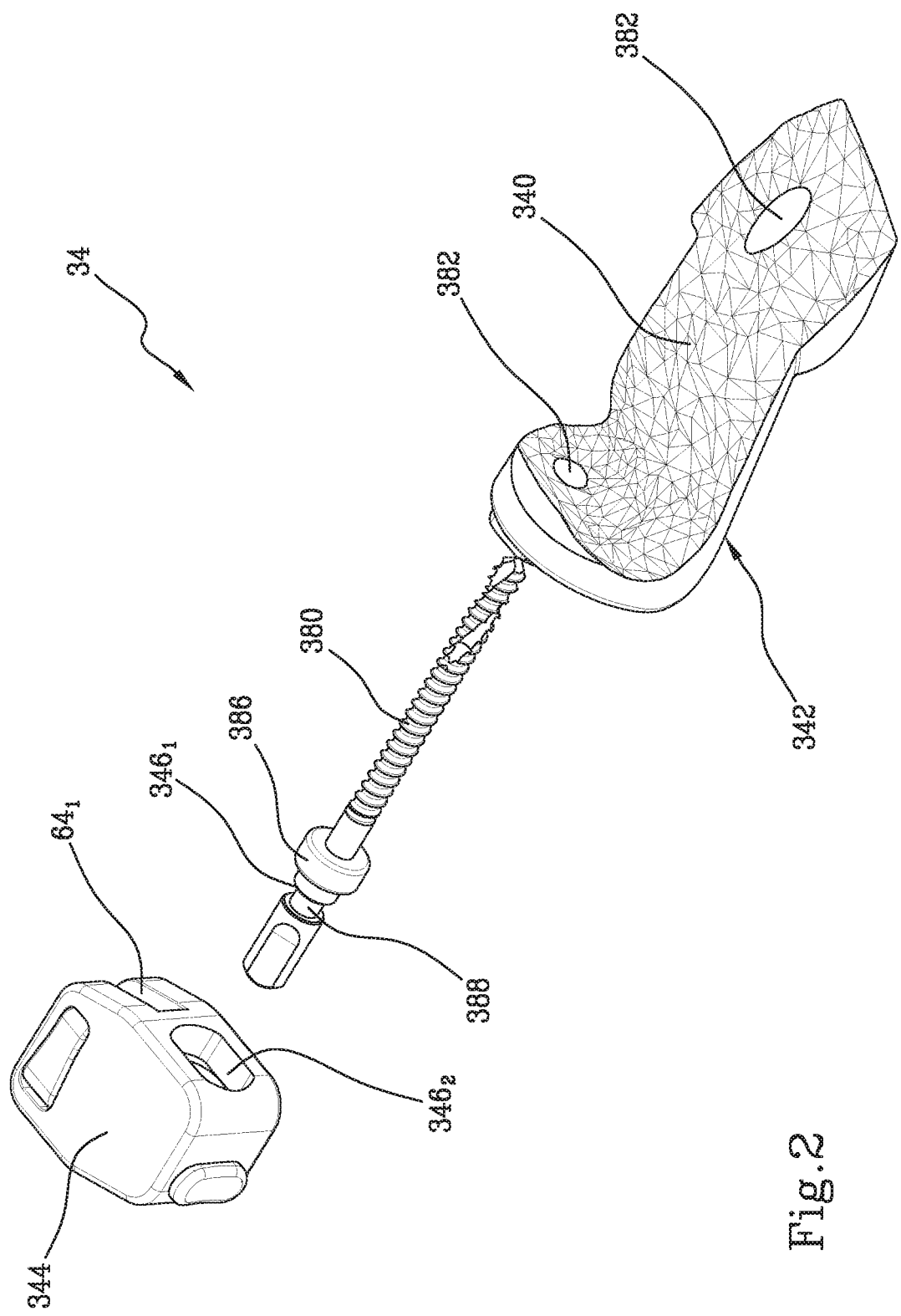
FIG. 2 shows an exploded view of the iliac unit of the alignment device of the invention, in a different position with respect to that in FIG. 1.

As the skilled person can easily see, the same considerations given above for the connecting portions 326 of the acetabular unit 32 apply, mutatis mutandis, for the connecting portions 346 of the iliac unit 34 as well (in this regard see also the detail in FIG. 2).

The following is a brief description of a method for conducting a periacetabular osteotomy operation using an alignment device 30 according to the invention.

The pre-surgery steps comprise:
Making a three-dimensional bone model of the iliac bone 80 of the patient.
Identifying a specific zone of the surface of the iliac bone 80 for fixing the acetabular unit 32.
Identifying the optimal insertion direction of at least one bone screw 380 in the previously identified zone of the surface of the iliac bone 80.
Designing the acetabular unit 32 in such a manner that the rest portion 320 is complementary to the previously identified zone of the surface of the iliac bone 80.

Designing the acetabular unit 32 in such a manner that it comprises at least one seat 382 that defines for the respective bone screw 380 the previously identified insertion direction.

Identifying a specific zone of the surface of the iliac bone 80 for fixing the iliac unit 34.

Identifying the optimal insertion direction of at least one bone screw 380 in the previously identified zone of the surface of the iliac bone 80.

Designing the iliac unit 34 in such a manner that the rest portion 340 is complementary to the previously identified zone of the surface of the iliac bone 80.

Designing the iliac unit 34 in such a manner that it comprises at least one seat 382 that defines the previously identified insertion direction for the respective bone screw 380.

Simulating on the three-dimensional bone model the periacetabular osteotomy in such a manner as to render the acetabulum 82 movable with respect to the remaining iliac bone 80.

Identifying the biomechanically correct position of the acetabulum 82 with respect to the remaining iliac bone 80.

On the base of the biomechanically correct position of the acetabulum 82 with respect to the remaining iliac bone 80, identifying the mutual correct position of the acetabular unit 32 and of the iliac unit 34.

Designing the bridge 36 in such a manner that it imposes the previously identified mutual correct position on the acetabular unit 32 and on the iliac unit 34.

Making the acetabular unit 32, the iliac unit 34, and the bridge 36 in accordance with the respective designs.

The surgery steps comprise:

Making the patient's iliac bone 80 accessible.

Placing the acetabular unit 32 on the previously identified zone of the surface of the iliac bone 80.

Providing at least one bone screw 380 in the at least one seat in the acetabular unit 32.

Fixing the acetabular unit 32 to the iliac bone 80 by means of the at least one bone screw 380.

Placing the iliac unit 34 on the previously identified zone of the surface of the iliac bone 80.

Providing at least one bone screw 380 in the at least one seat in the iliac unit 34.

Fixing the iliac unit 34 to the iliac bone 80 by means of the at least one bone screw 380.

Performing the periacetabular osteotomy so as to render the acetabulum 82 mobile with respect to the remaining iliac bone 80.

Moving the acetabulum 82 until it is in the previously identified bio-mechanically correct position.

Connecting the bridge 36 to the acetabular unit 32 and to the iliac unit 34.

Connecting the acetabulum 82 firmly to the remaining iliac bone 80.

Removing the bridge 36, the acetabular unit 32, and the iliac unit 34.

FIGS. 3 to 7 are briefly described below, with reference to an embodiment of the alignment device 30 according to the invention and to its use in a periacetabular osteotomy operation.

Figure 3:
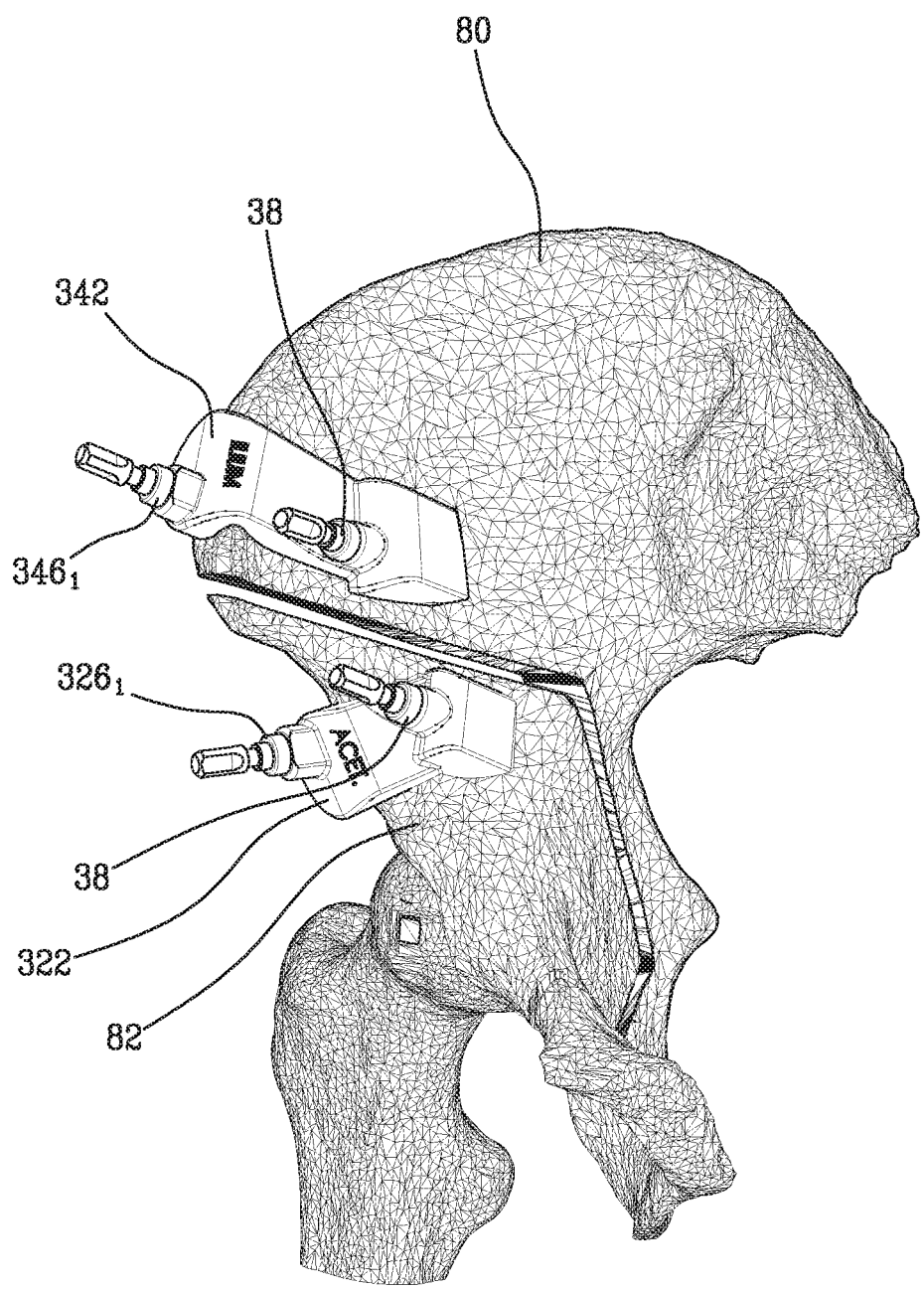
FIG. 3 shows a step in a periacetabular osteotomy operation in which, on an iliac bone, an alignment device of the invention is used, in a first configuration.

FIG. 3 shows a step in the operation in which, after having fixed the acetabular base 322 and the iliac base 342, the periacetabular osteotomy is performed in such a manner as to free the acetabulum 82.

Figure 4:
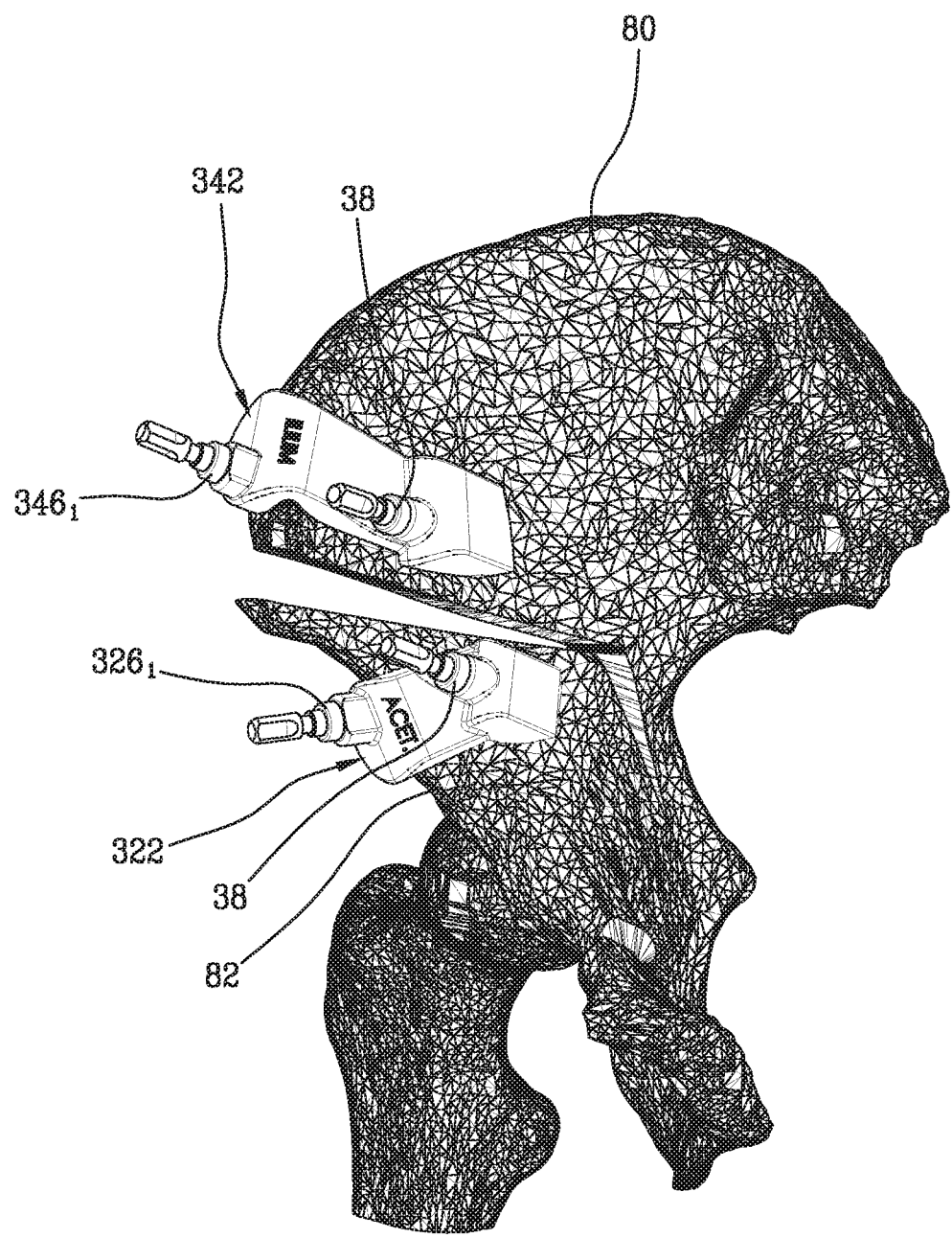
FIG. 4 shows a step in the operation in which the alignment device of the invention assumes a second configuration.

FIG. 4 shows a step in the operation, following that in FIG. 3, in which the acetabulum 82 is moved with respect to the remaining iliac bone 80.

Figure 5:
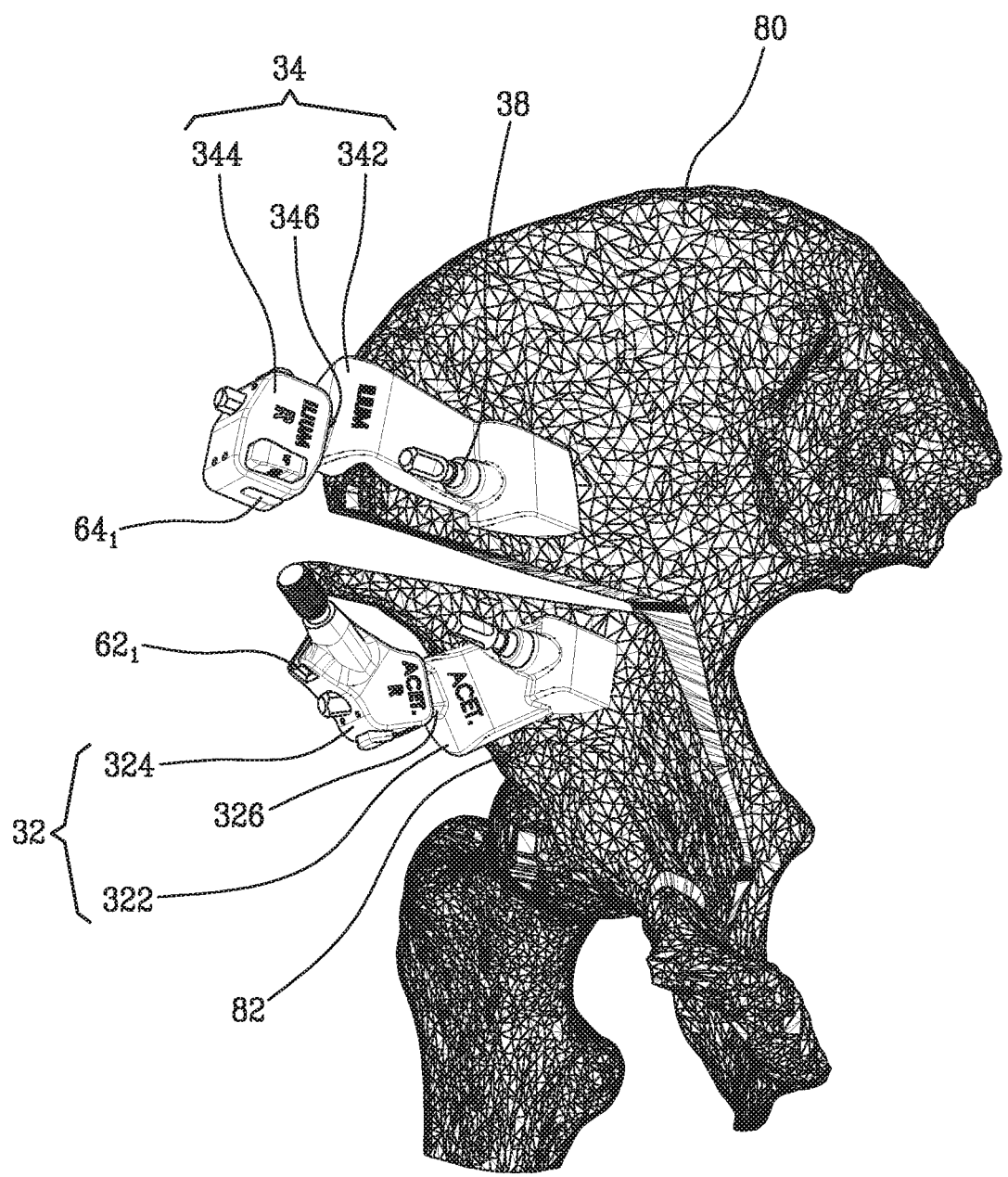
FIG. 5 shows a step in the operation in which the alignment device of the invention assumes a third configuration.

FIG. 5 shows a step in the operation, following that in FIG. 4, in which the acetabular base 322 is connected to the acetabular interface block 324, so as to form the acetabular unit 32; and the iliac base 342 is connected to the iliac interface block 344, so as to form the iliac unit 34.

Figure 6:
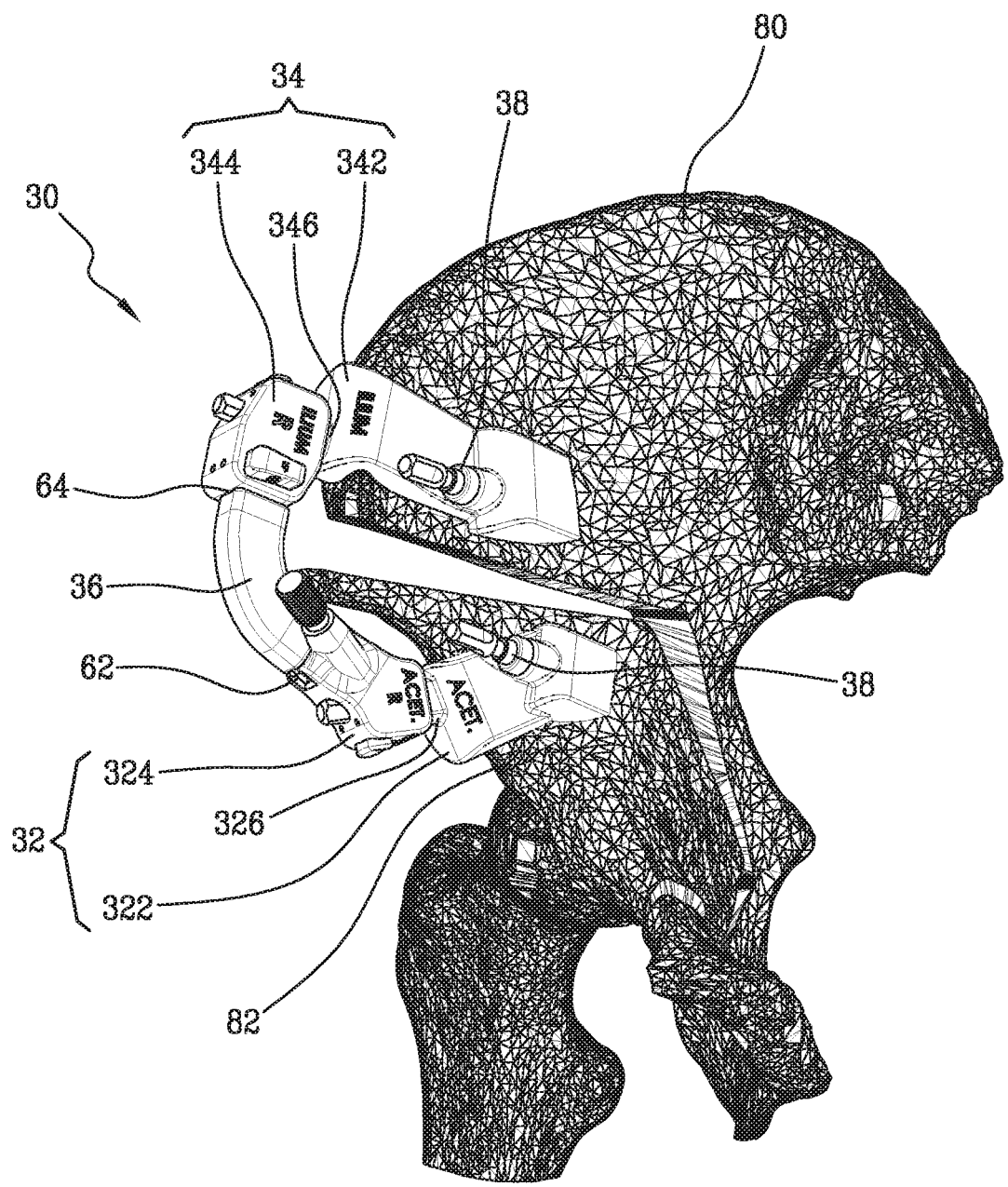
FIG. 6 shows a step in the operation in which the alignment device of the invention assumes a fourth configuration.

FIG. 6 shows a step in the operation, following that in FIG. 5, in which the bridge 36 is properly connected to the acetabular unit 32 and to the iliac unit 34 to ensure the bio-mechanically correct position of the acetabulum 82 with respect to the remaining iliac bone 80.

Figure 7:
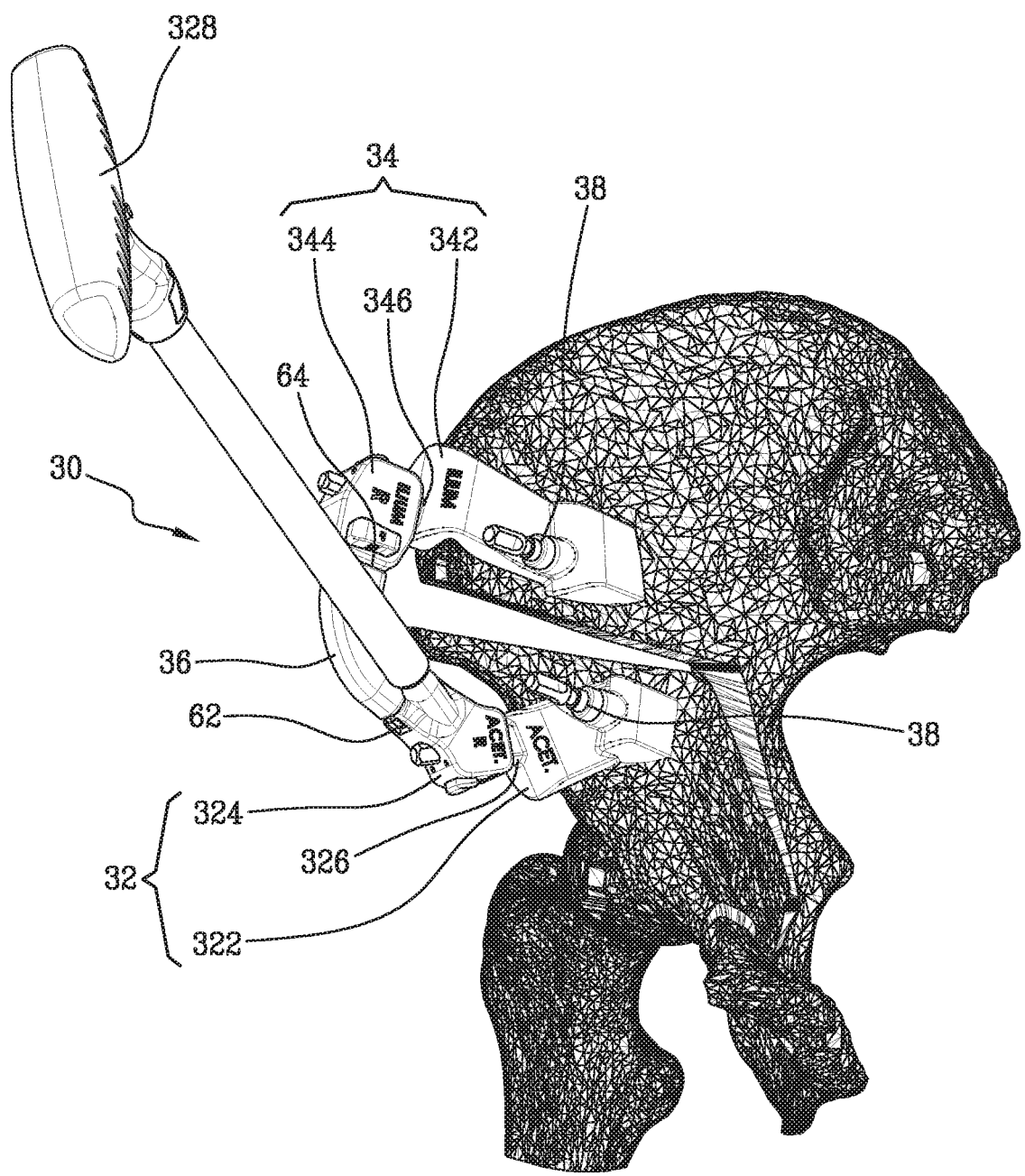
FIG. 7 shows a step in the operation similar to that in FIG. 6, in which the alignment device of the invention assumes an alternative configuration.

FIG. 7 shows a step in the operation, similar to that in FIG. 6, in which the removable handle 328 is mounted on the acetabular unit 32 to facilitate the movement of the acetabulum 82.

As the skilled person can well understand, the invention enables the drawbacks highlighted above with reference to the prior art to be overcome.

In particular, the present invention provides a device 30 for periacetabular osteotomies that facilitates the surgeon during the re-alignment.

In addition, the present invention provides a device 30 for periacetabular osteotomies that minimizes risks for the patient due to human error.

Finally, the present invention provides a device 30 for periacetabular osteotomies that allows the surgeon to speed up the operating times.

It is clear that the specific features are described in relation to different embodiments of the invention with the intention of providing non-limiting examples. A person skilled in the art can obviously make further modifications and variations to the present invention, in order to satisfy contingent and specific needs. For example, the technical features described in relation to an embodiment of the invention may be extrapolated from it and applied to other embodiments of the invention. These modifications and variations are also included within the invention's scope of protection, as defined by the following claims.

The invention claimed is:

1. An alignment device for carrying out a periacetabular osteotomy operation on a predefined patient, comprising:
a patient-specific acetabular unit, suitable for being fixed in a univocal position on an iliac bone of the predefined patient, in proximity of an acetabulum of a femur;
a patient-specific iliac unit, suitable for being fixed in a univocal position on the iliac bone of the predefined patient, in a lateral position with respect to the patient-specific acetabular unit;
a patient-specific bridge, suitable for being connected in a rigid and univocal manner to the patient-specific acetabular unit and to the patient-specific iliac unit;
wherein, when the patient-specific acetabular unit and the patient-specific iliac unit are properly fixed on the iliac bone, the patient-specific acetabular unit and the patient-specific iliac unit assume, the one with respect to the other, a first predefined mutual position incompatible with a simultaneous connection of the patient-specific bridge to both said units; and
when osteotomy is carried out and the patient-specific bridge is connected both to the patient-specific acetabular unit and to the patient-specific iliac unit, the patient-specific acetabular unit and the patient-specific iliac unit assume, the one with respect to the other, a second predefined mutual position, different from the first mutual position and corresponding to a bio-mechanically correct position of the acetabulum with respect to a remaining portion of the iliac bone.

2. The device according to claim 1, wherein the patient-specific bridge comprises an acetabular end and an iliac end, wherein the acetabular end of the patient-specific bridge and the patient-specific acetabular unit respectively comprise first and second constraint means complementary to one another and suitable for creating a mutual rigid and univocal constraint, and wherein the iliac end of the patient-specific bridge and the patient-specific iliac unit respectively comprise third and fourth constraint means complementary the one to the other and suitable for creating a mutual rigid and univocal constraint.

3. The device according to claim 2, wherein the patient-specific iliac unit comprises the fourth constraint means and a patient-specific rest portion, complementary to a specific zone of a surface of the iliac bone.

4. The device according to claim 3, wherein the patient-specific iliac unit comprises:
an iliac base comprising the patient-specific rest portion and a connecting portion, and
a general use iliac interface block comprising the fourth constraint means and a connecting portion, and
wherein the connecting portion of the iliac base and the connecting portion of the iliac interface block are suitable for being connected to one another in a rigid and univocal manner.

5. The device according to claim 3, wherein the patient-specific acetabular unit comprises:
an acetabular base comprising the patient-specific rest portion and a connecting portion, and
a general use acetabular interface block comprising the second constraint means and a connecting portion, and
wherein the connecting portion of the acetabular base and the connecting portion of the acetabular interface block are suitable for being connected the one to the other in a rigid and univocal manner.

6. The device according to claim 2, wherein the patient-specific acetabular unit comprises the second constraint means and a patient-specific rest portion, complementary to a specific zone of a surface of the iliac bone.

7. The device according to claim 6, wherein the patient-specific acetabular unit comprises:
an acetabular base comprising the patient-specific rest portion and a connecting portion, and
a general use acetabular interface block comprising the second constraint means and a connecting portion, and
wherein the connecting portion of the acetabular base and the connecting portion of the acetabular interface block are suitable for being connected the one to the other in a rigid and univocal manner.

8. The device according to claim 6, wherein the patient-specific iliac unit comprises the fourth constraint means and a patient-specific rest portion, complementary to a specific zone of a surface of the iliac bone.

9. The device according to claim 8, wherein the patient-specific rest portion of the patient-specific acetabular unit and/or the patient-specific rest portion of the patient-specific iliac unit are at least partially concave.

10. The device according to claim 8, wherein the patient-specific iliac unit comprises:
an iliac base comprising the patient-specific rest portion and a connecting portion, and
a general use iliac interface block comprising the fourth constraint means and a connecting portion, and
wherein the connecting portion of the iliac base and the connecting portion of the iliac interface block are suitable for being connected to one another in a rigid and univocal manner.

11. The device according to claim 8, wherein the patient-specific acetabular unit comprises:
an acetabular base comprising the patient-specific rest portion and a connecting portion, and
a general use acetabular interface block comprising the second constraint means and a connecting portion, and
wherein the connecting portion of the acetabular base and the connecting portion of the acetabular interface block are suitable for being connected to each other in a rigid and univocal manner.

12. The device according to claim 11, wherein the patient-specific iliac unit comprises:
an iliac base comprising the patient-specific rest portion and a connecting portion, and
a general use iliac interface block comprising the fourth constraint means and a connecting portion, and
wherein the connecting portion of the iliac base and the connecting portion of the iliac interface block are suitable for being connected to one another in a rigid and univocal manner.

13. The device according to claim 12, wherein the constraint means between the patient-specific bridge and the patient-specific acetabular unit and/or the patient-specific iliac unit comprise shape couplings, releasable by means of snap mechanisms.

14. The device according to claim 13, wherein the connecting portions between the acetabular base and the acetabular interface block and/or the connecting portions between the iliac base and the iliac interface block, comprise shape couplings, releasable by means of snap mechanisms.

15. The device according to claim 14, wherein the shape couplings of the constraint means and/or of the connecting portions are different from one another and mutually incompatible.

16. The device according to claim 12, wherein the connecting portions between the acetabular base and the acetabular interface block and/or the connecting portions between the iliac base and the iliac interface block, comprise shape couplings, releasable by means of snap mechanisms.

17. The device according to claim 1, wherein the patient-specific iliac unit and/or the patient-specific acetabular unit comprise fixing means, suitable for fixing each unit on the iliac bone.

18. The device according to claim 17, wherein the fixing means comprises at least one bone screw and at least one seat suitable for receiving the bone screw.

19. The device according to claim 1, wherein the patient-specific acetabular unit comprises a removable handle.

20. A method for preparing a periacetabular osteotomy operation using an alignment device according to claim 1, comprising the following pre-surgery steps:
making a three-dimensional bone model of the iliac bone of the predefined patient;
identifying a specific zone of a surface of the iliac bone for fixing the patient-specific acetabular unit;
identifying an optimal insertion direction of at least one acetabular unit bone screw in the previously identified specific zone of the surface of the iliac bone for fixing the patient-specific acetabular unit;
designing the patient-specific acetabular unit in such a manner that a rest portion of the patient-specific acetabular unit is complementary to the previously identified specific zone of the surface of the iliac bone for fixing the patient-specific acetabular unit;

designing the patient-specific acetabular unit in such a manner that the patient-specific acetabular unit comprises at least one acetabular unit seat which defines for the at least one acetabular unit bone screw the previously identified optimal insertion direction of the at least one acetabular unit bone screw;

identifying a specific zone of the surface of the iliac bone for fixing the patient-specific iliac unit;

identifying an optimal insertion direction of at least one iliac unit bone screw in the previously identified specific zone of the surface of the iliac bone for fixing the patient-specific iliac unit;

designing the patient-specific iliac unit in such a manner that a rest portion of the patient-specific iliac unit is complementary to the previously identified specific zone of the surface of the iliac bone for fixing the patient-specific iliac unit;

designing the patient-specific iliac unit in such a manner that the iliac unit comprises at least one iliac unit seat which defines for the at least one iliac unit bone screw the previously identified optimal insertion direction of the at least one iliac unit bone screw;

simulating on the three-dimensional bone model the peri-acetabular osteotomy so as to render the acetabulum movable with respect to the remaining portion of the iliac bone;

identifying a biomechanically correct position of the acetabulum with respect to the remaining portion of the iliac bone;

on the base of the biomechanically correct position of the acetabulum with respect to the remaining portion of the iliac bone, identifying a mutual correct position of the patient-specific acetabular unit and of the patient-specific iliac unit;

designing the patient-specific bridge in such a manner that the patient-specific bridge imposes the previously identified mutual correct position on the patient-specific acetabular unit and on the patient-specific iliac unit; and making the patient-specific acetabular unit, the patient-specific iliac unit and the patient-specific bridge in accordance with the respective designing steps.

* * * * *